(12) United States Patent
Baumoel (10) Patent No.: US 6,442,999 B1
(45) Date of Patent: Sep. 3, 2002

(54) LEAK LOCATOR FOR PIPE SYSTEMS

(76) Inventor: Joseph Baumoel, 104 Fairway View Dr., The Hamlet, Commack, NY (US) 11725

( * ) Notice: Subject to any disclaimer, the term of this patent is extended or adjusted under 35 U.S.C. 154(b) by 0 days.

(21) Appl. No.: 09/815,099

(22) Filed: Mar. 22, 2001

(51) Int. Cl.[7] .......................... G01M 3/00; G01M 3/24; G08B 29/00; G01F 1/66
(52) U.S. Cl. ...................... 73/40.5 A; 73/49.5; 73/592
(58) Field of Search .......................... 73/40.5 A, 40, 73/49.1, 49.5, 592

(56) References Cited

U.S. PATENT DOCUMENTS

| 4,043,180 A | * | 8/1977 | Morris et al. ............. 73/40.5 A |
| 4,372,151 A | * | 2/1983 | Muraview et al. ........ 73/40.5 A |
| 4,856,321 A | * | 8/1989 | Smalling et al. .......... 73/40.5 A |
| 4,858,462 A | * | 8/1989 | Coulter et al. ............ 73/40.5 A |
| B34,083,229 A | * | 7/1990 | Anway ..................... 73/40.5 A |
| 5,038,614 A | * | 8/1991 | Bseisu et al. .................. 73/592 |
| 5,058,419 A | * | 10/1991 | Nordstrom et al. ....... 73/40.5 A |
| 5,117,698 A | | 6/1992 | Baumoel ................. 73/861.28 |
| 5,548,530 A | * | 8/1996 | Baumoel ..................... 364/509 |
| 5,623,421 A | * | 4/1997 | Savic ......................... 364/510 |
| 5,974,862 A | * | 11/1999 | Lander et al. ........... 73/40.5 A |
| 5,987,990 A | * | 11/1999 | Worthington et al. ......... 73/592 |
| 6,128,946 A | * | 10/2000 | Leon et al. ..................... 73/46 |

* cited by examiner

Primary Examiner—Hezron Williams
Assistant Examiner—David J. Wiggins
(74) Attorney, Agent, or Firm—F. Chau & Associates, LLP (57) ABSTRACT

A system and method for determining a time of occurrence of a pressure wave in a pipe provides a first sonic transducer and a second sonic transducer at each of a plurality of site locations along a pipe. Sonic waves are generated through a pipewall at a known desired rate. At each of the plurality of site locations, the sonic waves travel from the first sonic transducer to the second sonic transducer through a liquid flow in the pipe. A measure of travel time is set for the sonic waves. The measure is compared to each of the successive travel times for the sonic waves as the sonic waves arrive at the respective second transducers. A string of counts is output at each second transducer. Each count includes a first count value if a present sonic wave has a travel time that is late as compared to the measure. A time of occurrence of the pressure wave is determined based on a reference clock when the string of counts includes a string of first count values longer than a threshold value. The time of occurrence of a pressure transient is indicated by a first count in the string of first count values.

20 Claims, 6 Drawing Sheets

LEAK LOCATOR FOR PIPE SYSTEMS

BACKGROUND

1. Technical Field

This disclosure relates to sensing systems and more particularly, to a system for sensing a location of a leak in a pipeline system.

2. Description of the Related Art

It is common practice to install liquid and gas pipelines underground or underwater, both to defeat the possibility of tampering, and as may be necessary for regulatory or logistical reasons (e.g., passing under a river). In such cases, when a leak occurs, the actual source of the leak may not be visible. Under such a circumstance, remediation of the leak, once detected by other means, will not be possible until the actual source is located.

Since time is of the essence when remediation is required, to limit the amount of the spill, a system that identifies the location is essential. Since pipelines can run through difficult terrain, such as underwater or in jungle areas, knowing the exact location is a significant factor in permitting fast remediation. High precision avoids the need for time consuming digging of substantial amounts of territory to find the leak.

It is well known that pipelines are under some degree of pressure, either from the pumping of the gas or liquid, or by the effect of gravity. Accordingly, when a pipeline ruptures, it is generally accompanied by the reduction of pressure at the point of the leak. This generates a low-pressure wave that travels in both directions, at the speed of sound in the medium, plus or minus the effect of actual flow rate in the downstream and upstream directions respectively.

In pipeline systems, which may extend over many miles or just a few hundred feet, it is necessary and often imperative to be able to accurately detect the location of a leak. Leaking pipes may cause dangerous conditions, or environmental issues if not properly addressed in an expedient manner.

In the transport of hydrocarbons, such as oil, leaks may be detected at monitoring stations, which are distributed at intervals along the pipeline. Changes in pressure or flow rate are detected and anomalies are determined to determine leaks in the pipeline. Pressure changes are determined between monitoring stations; however, with conventional detection systems when the leak has first occurred is not known. Accordingly, location of the leak is difficult to determine with the accuracy needed for a quick response. With conventional systems, a leak's location can be determined in a region on the order of hundreds of meters (e.g., 150 to 200 meters).

Therefore, a need exists for a system and method for accurately determining the location and time of occurrence of a leak in a pipeline system.

SUMMARY OF THE INVENTION

A system and method which defines the location in a pipeline, at which a leak has occurred, with very high precision, using the detection of the low-pressure wave resultant from the leak is disclosed. The low-pressure wave travels at the speed of sound in the liquid or gas in the pipeline in both upstream and downstream directions. Site stations that can detect the arrival time of the pressure wave are located at opposite ends of the pipeline segment. The Site Stations detect the arrival time of the low-pressure wave non-intrusively, and with great precision.

Transmission of the sensed data to a master station permits the computation of the location to within the precision permitted by the time resolution that the low-pressure wave is detected. A global positioning system (GPS) mapping system is employed to permit rapid access to the site of the leak by either helicopter, truck or boat, as may be appropriate.

A system and method for determining a time of occurrence of a pressure wave in a pipe provides a first sonic transducer and a second sonic transducer at each of a plurality of site locations along a pipe. Sonic waves are generated through a pipewall at a known desired rate. At each of the plurality of site locations, the sonic waves travel from the first sonic transducer to the second sonic transducer through a liquid flow in the pipe. A measure of travel time is set for the sonic waves. The measure is compared to each of the successive travel times for the sonic waves as the sonic waves arrive at the respective second transducers. A string of counts is output at each second transducer. Each count includes a first count value if a present sonic wave has a travel time that is late as compared to the measure.

A time of occurrence of the pressure wave is determined based on a reference clock when the string of counts includes a string of first count values longer than a threshold value. The time of occurrence of a pressure transient is indicated by a first count in the string of first count values. The time of occurrence is employed in accurately calculating the position of a leak, hot tap or malfunctioning valve, pump, etc.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

The present invention includes a system and method for measuring pressure transients in a flow within a pipe. The present invention provides a new and very precise way of locating the place where a leak has occurred on a pipeline, which transports liquids, such as hydrocarbons or other types of liquid. Advantageously, the present invention provides a precision of less than several meters, and preferably, under 1 meter is determining the location of a leak.

Figure 1:
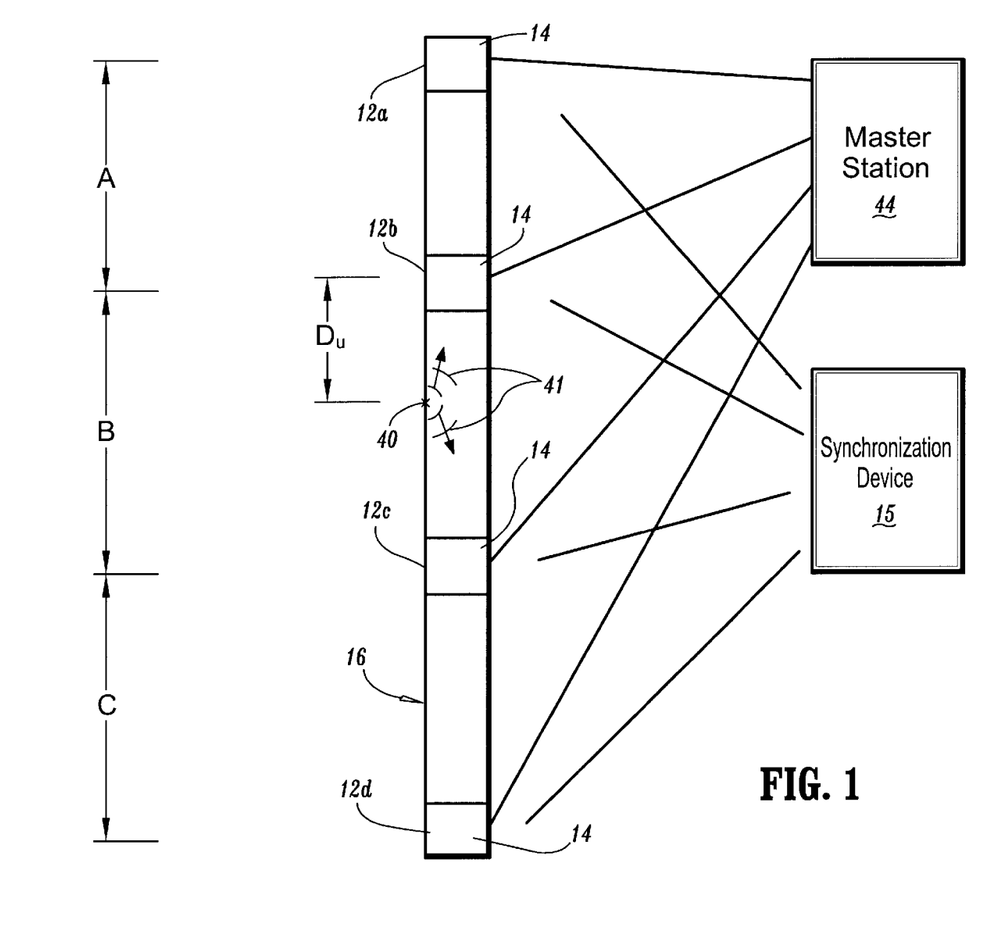
FIG. 1 is a schematic diagram of a pipe system having a leak detection system installed in accordance with the present invention.

Referring now in specific detail to the drawings in which like reference numerals identify similar or identical elements throughout the several views, and initially to FIG. 1, a pipeline system 10 is shown in accordance with one embodiment of the present invention. System 10 includes a plurality of monitoring or site stations 12a–12d, generally referred to as site stations 12 hereinafter, which monitor occurrences within pipe system 10. In the embodiment shown, site stations 12 each preferably include a wide beam transit-time ultrasonic flow meter 14, as described in U.S. Pat. No. 5,117,698, incorporated herein by reference. Flow meter 14 may include a clamp-on type, which clamps to an exterior wall of a pipe 16 to permit flow characteristics to be measured in pipe 16. Flow meters 14 may be adapted to monitor flow characteristics at site stations 12.

Distances of segments A, B, C, etc. as shown in FIG. 1 are known. This information will be used to locate leaks as will described below.

Figure 2:
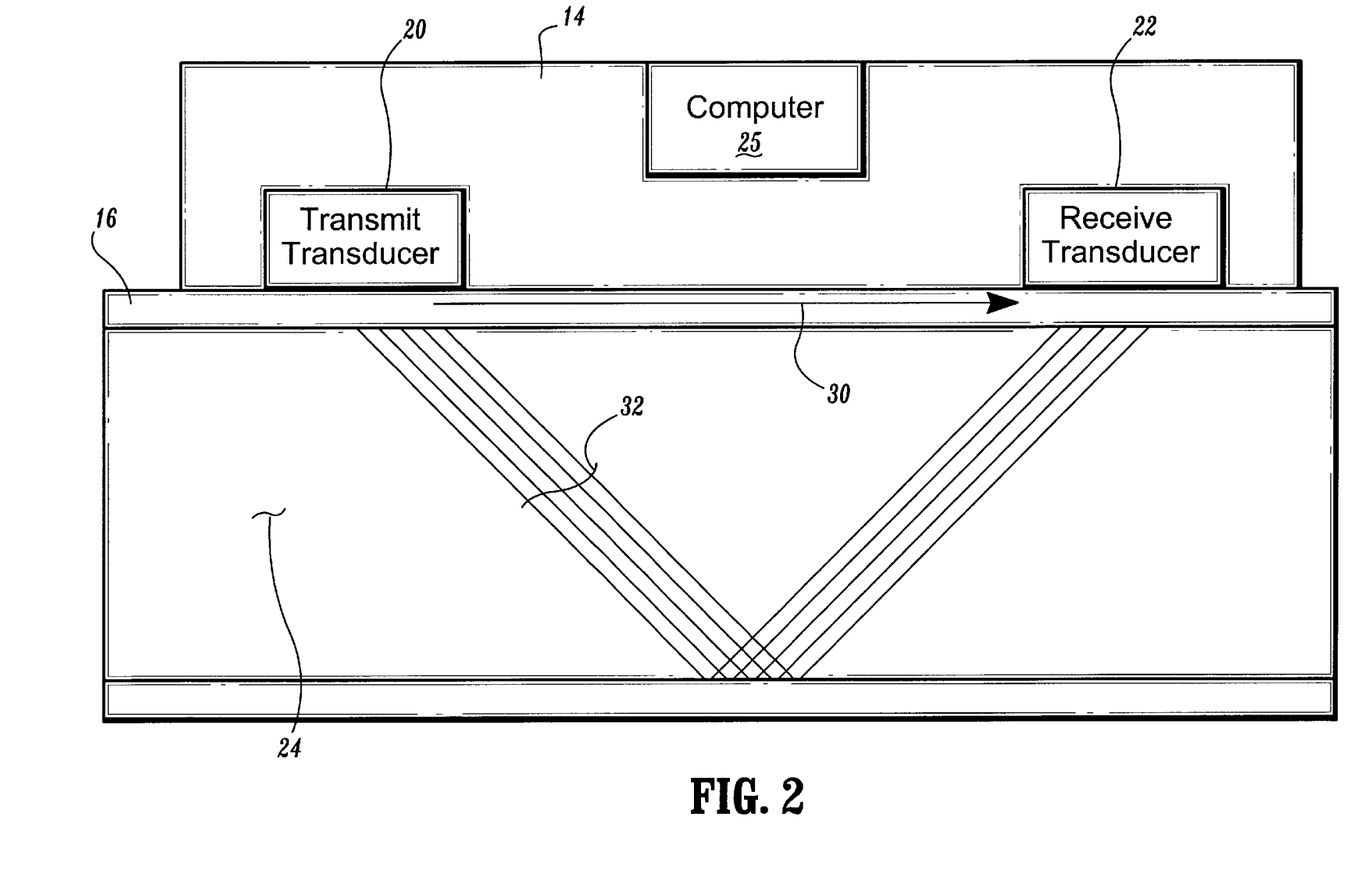
FIG. 2 is a cross-sectional view of the pipe system of FIG. 1 showing greater detail of sonic energy waves traveling in the pipe at a site station in accordance with the present invention.

Referring to FIG. 2, clamp-on wide beam transit-time ultrasonic flow meter 14 includes a set of ultrasonic transducers. A transducer 20 is employed to transmit wide beam ultrasonic signals into pipe 16 and flow 24. A transducer 22 is employed to receive wide beam ultrasonic signals from pipe 16 and flow 24. The transmitted sonic energy in the form of a wide beam 26 travels across pipe 16 and is measured by transducer 22. A computer or data acquisition device 25 may be employed with flow meter 14 to perform computations to determine flow rates, proportions of the constituents material of flow 24, storing lookup tables or other parameters needed to determine characteristics of flow 24.

A natural mode of sonic energy transmission is excited in pipe 16, in which a transverse wave 30 travels axially down the pipe wall at the velocity characteristic of the pipe's material, and at a frequency dependent on the pipe material and a wall thickness "t". When such a wave 30 is generated, as it travels down the pipe wall, wave 30 radiates a sonic wave 32 into the flow 24, which ultimately reflects off the far wall and reenters the pipe wall on the same side of the pipe from which is was originally transmitted. The sonic energy then enters this receive transducer 22 and generates a receive signal.

Referring FIGS. 1 and 2, one principle of operation for the present invention is the detection of the change in liquid density associated with the lowering of pipeline pressure caused by a leak at, e.g., location 40. This low-density transient wave 41 propagates both upstream and downstream from the point of the leak at the velocity at which sound travels through the liquid(s). When these transient waves arrive at an upstream measuring station 12b, measuring station 12b records the transient with a time resolution of, e.g., between 1 and 2 milliseconds for a transmission rate of about 1000 pulses per second.

Clamp-on ultrasonic flowmeter 14 senses the sonic propagation velocity of the medium in pipe 16. It does so by measuring the time that it takes for a sonic pulse 32 to travel over a known path length through the medium, generally a diagonal path from the transmitting transducer 20 that reflects diagonally from the opposite side of the pipe to be detected by the receive transducer 22.

Since the sonic velocity of liquid media 24 is dependent on the density of the liquid, and the density of the liquid is a function of the pressure, it is seen that detection of a change in sonic propagation velocity is a means of detecting relative pressure itself. Accordingly, the clamp-On ultrasonic flowmeter 14 has the ability to sense the change in pressure caused by a leak, as the pressure wave arrives from the point of the leak, traveling at the speed of sound, to the location of the flowmeter site station 12 (FIG. 1). Since it is not required that the site station measure flow, a freestanding ultrasonic pressure wave detector may be employed in an alternate embodiment.

The monitoring of the flow (density) is performed at each measuring station 12a, 12b, 12c, etc.). Each measuring site station 12 is synchronized by a common clock or synchronization device 15. For example, synchronization device 15 may include a zero latency communication system, WWV or global positioning system (GPS) technology. A synchronizing pulse is sent to or maintained at each station 12. The common clock signal provides a frame of reference for a leak detection position as will be described in detail below.

It may be seen that any spurious high frequency transients, whose wavelength is shorter than the sonic beam path length, will have their effect integrated out of the detection range of the ultrasonic pressure wave detector of the present invention. Since, in a pipe of, say, 12 inches diameter, filled with, say, Crude Oil, the path length is about one meter, and the sonic propagation velocity can be, say, 1400 meters per second, any spurious wave with a frequency of higher than about 1400 Hz will be filtered out. But, since the low pressure wave caused by a pipe rupture will generally have a rise time of more than 1 millisecond, (an equivalent frequency of below 1000 Hz), the system described will be able to detect the transient change of sonic propagation velocity caused by a leak induced low pressure wave, and be free of the disruptive effects of anomalous pressure waves endemic to a pipeline.

Since the sonic propagation velocity of the liquids of interest lie in the range of from about 700 to 1500 meters per second, to locate the leak within one meter would provide that sensing the arrival of the transient at each of the segment's site stations 12 with a time resolution of about 1 millisecond. Accordingly, a site station 12 includes a means of generating a sonic interrogation pulse into the pipeline at least every millisecond. On reception of the sonic pulse, it will be determined how long it took for the pulse to arrive, from the time of its transmittal.

In one embodiment, at a repetition rate of about, for example, 1 to 2 milliseconds, each site station 12 transmits ultrasonic pulses into the pipe wall by use of wide beam clamp-on transducer 20. This pulse enters the liquid and travels in such a way as to ultimately pass through the pipe wall and reflect back to the side of transducer 22. The pipewall acts as a beam splitter, splitting the ultrasonic beam between the pipewall and the flow. Transducer 22 detects the ultrasound pulse and conveys a signal (receive signal) at site stations 12. The arrival time of the signal depends on the sonic propagation velocity of the liquid flow 24 in pipe 16. Sonic propagation velocities of sound in liquids are a function of the liquid's density. Since the arrival of a low-density wave will lower the sonic velocity measured at the transducer location, the arrival time of the sonic pulses will be suddenly extended. The extension of the sonic pulses is employed in the present invention to accurately determine the time of occurrence of the leak (or drop in pressure) and the location of the leak.

Site station 12 amplifies the received transducer signal and digitizes its arrival time, e.g., relative to the travel time of the previously transmitted sonic pulse. A time reference or measure (see FIG. 3) is established for the arrival time of the signal prior to the arrival of a low-density (e.g., leak transient) wave. The reference is created by setting a reference in normal or stable flow conditions. Thus, when a low-pressure wave arrives, signifying a leak, site stations 12 are in a position to notice the sudden delay in arrival time of a received sonic signal.

The receive signal may have a "marker" embedded in the receive signal or a portion of the receive signal may be employed as a reference which is used as a discrete time location to be compared to a measure value. If the liquid sonic velocity is changing due to chemical or temperature causes, such density or sonic velocity changes are much slower than pressure transient causes, and so the alternate late or early outputs will occasionally see an extra late or early output to move the window so as to follow the slow time movement of the signal. The extra signals can be averaged out over time.

When a low-pressure transient caused by a leak arrives, the time of the signal is suddenly changed by an amount dependent on the actual degree of the pressure of the density change. In such a case, it will take a number of successive late counts before a new average value is determined (before the Measure is stabilized).

Figure 3:
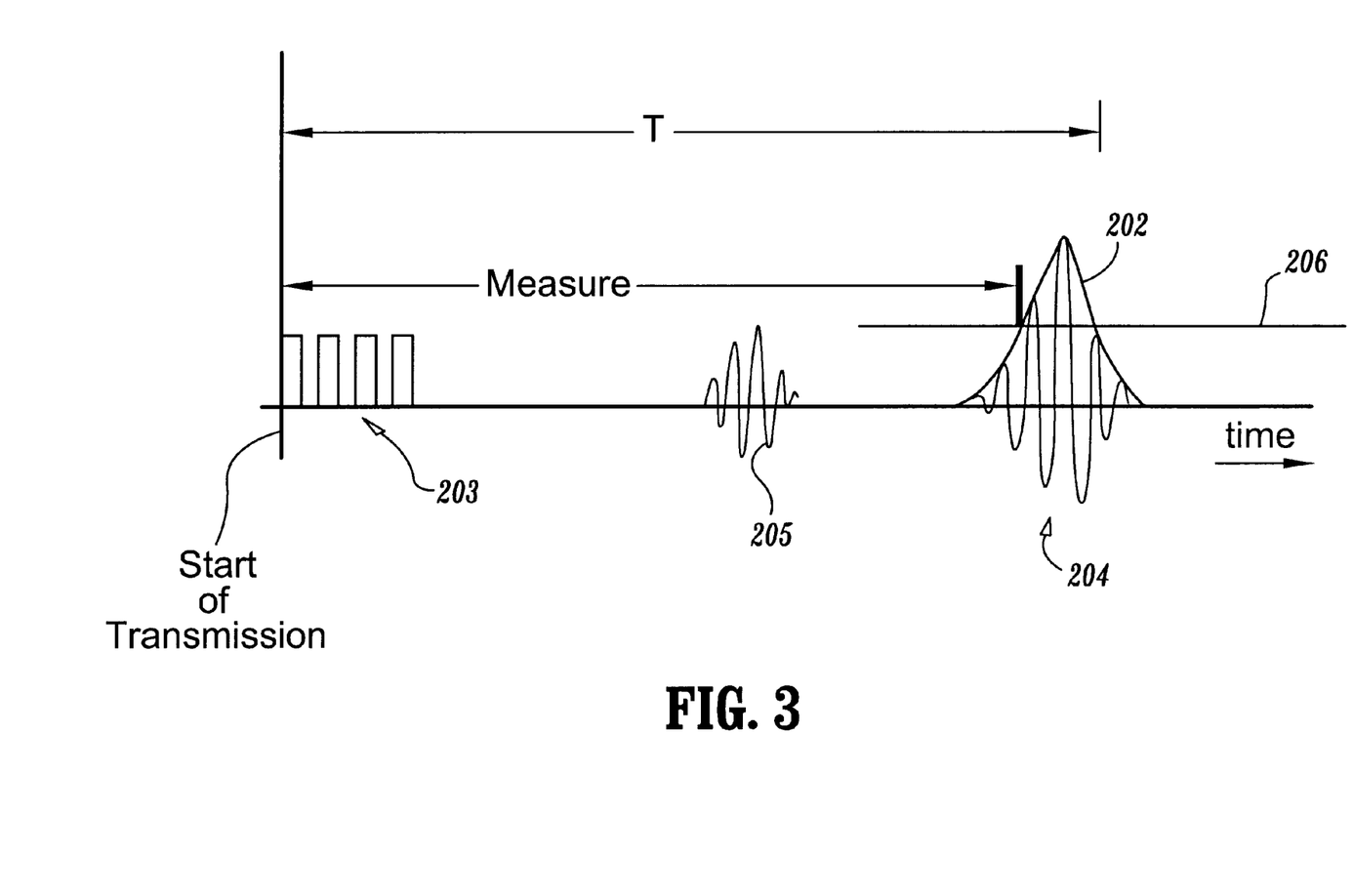
FIG. 3 depicts a time line of signals generated by transducers of FIG. 2 in accordance with the present invention.

Referring to FIG. 3, an example of a late count is shown. The transmission of sonic wave 32 (FIG. 1) or signal 203 produces a pipe wall signal 205 (wave 30 in FIG. 1). Envelope 202 breaks a threshold line 206 at a point 207 beyond a threshold or measure time (labeled "Measure" in FIG. 3). Site station 12 (FIG. 1) records the successive late/early counts and divides the counts into bit words. When a synchronizing pulse arrives at, e.g., one-minute intervals, site station 12 transmits these words sequentially to a master station 44. If there are 1,000 transmit pulses per second, in one minute there will have been 60,000 transmit pulses at the time that the next synchronizing pulse arrives. This provides that, at a 16-bit word density, 3750 16-bit bytes are be transmitted to master station 44.

A threshold line 206 in FIG. 3 or other reference may be employed to define a position where signal 204 first arrived. The beginning of this sloped line or "cusp" marks the arrival time of the low-pressure wave in this example, however other references may be selected.

Wide beam ultrasonic transducers 20 and 22 of FIG. 2 operate as exciters of the pipe's sonic waveguide properties. These are dependent on the pipe's wall thickness and material, which together determine the desired frequency and phase velocity of the transducer. In one embodiment, with a transmittal form transducer 20 of from 3 to 5 pulses shown as signal 203, a very large and "low Q" (fast response) envelope 202 is preferably generated at transducer 22. The signal 204 may be fully rectified or subjected to other wave shaping processes. The arrival time T of the signal 204 is detected by digitally imaging the very sharp (low Q) shape of the received signal, and then using digital computation to analyzing the wave shape to identify the arrival time T of the very first "cusp" of the received signal 204.

This arrival time T is digitally represented and fed into a register or other storage device, after being averaged, for example exponentially averaged. Exponential averaging, in one embodiment is performed by subtracting the currently sensed arrival time T(current) from the previously exponentially averaged arrival time T(previous) and dividing the result by a large number, say from 3 to 10. The result of the division is then added or subtracted from a result of a prior exponential average (or previously assigned number) to establish a new average to be used for the next transmission. This has the effect of establishing a relatively stable value representing the arrival time for the current liquid under nominal conditions.

The averaged number or stored register number is a measure value (Measure in FIG. 3) against which the next arrival time T will be compared. When each new pulse is received, along with adjusting the exponential average, a determination is made whether the latest pulse is later or earlier than the average previously established. In one embodiment, a pulse with an arrival time (T) later than the Measure is coded as a "1" in a FIFO, and earlier is coded as a "0". Thus, a FIFO may empty its contents by transmitting the contents to a master station 44 (FIG. 1) or other reporting location, which will store the history of Early/Late results of the transmissions.

If the sonic velocity of the liquid changes, say due to changes in liquid chemistry, temperature or pressure not associated with leaks, the history of ones and zeroes will register this gradual change by a small excess of ones or zeroes until a new stable average is established. However, this process is much slower than the very fast change in sonic propagation velocity caused by a leak. Accordingly, it should be possible to distinguish a true leak from other causes for a change in sonic propagation velocity. These other changes may be characterized and identified in the history of late/early determinations at master station 44. Such changes may include opening a valve, activating a pump, etc.

When a leak occurs, and the pressure wave arrives at site station 12 (FIG. 1), the leading edge of that change from a higher to a lower pressure is instantaneously effective in reducing the sonic propagation velocity at that location. Accordingly, the first report after its arrival will be a "1". In fact, since an exponential average divider will be chosen so the Average will only change slowly, all the transmissions following the arrival of the pressure wave will be ones, until the exponential average has had time to establish a new average, associated with the new lower post-leak pressure.

The contents of the FIFO are periodically sent to master station 44, in a time-synchronized fashion. They are preferably grouped into digital words and then compressed, so that, for example, the 60,000 ones or zeros collected in a one minute period, assuming a 1 millisecond pulse transmit rate, can be represented in about 500 bytes.

Figure 4:
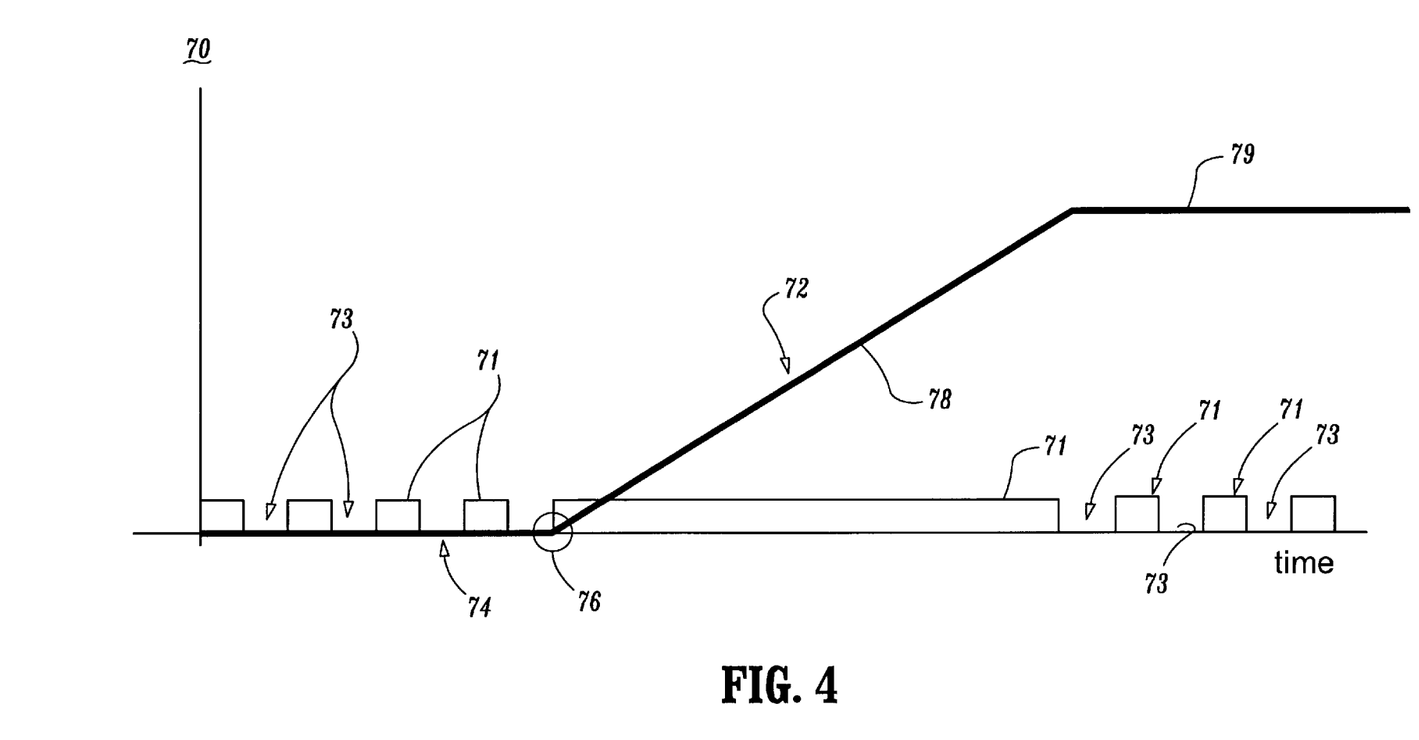
FIG. 4 shows a plot in accordance with the present invention indicating one and zero reports to establish when a leak has occurred.

Referring to FIG. 4, master station 44 (FIG. 1) may include a computer or other monitoring device which creates a display 70 in which, for example, each site station's data is displayed as a result of an integration or cumulative sum. Display 70 shows integrated ones 71 and zeros 73 for a site station for a given synchronized time (e.g., one minute or other set amount of time) as a plot 72.

If a one is integrated as a height increase, and a zero as a height decrease, on data plot 72, then when, on the average there are as many ones as zeroes, plot 72 will be a relatively flat line 74, near zero. If there is a leak, starting at the display time 76 that site station first started to receive the continuous ones caused by a leak, display 70 shows an integration of the ones, forming a linearly rising line 78 until a new average 79 is achieved. This permits identification of the exact time that the low-pressure transient arrived, to the millisecond. This also permits location of a leak to the order of magnitude of about 1 meter or better, dependent only on signal to noise ratio of the signal. Rising line 78 indicates a leak. Master station 44 may include characteristic curve data, which is compared to the sit station data to determine a leak. The duration and sizes of the plots can be compared to a reference value(s) or threshold to determine the severity or type of leak.

The characteristic display of a leak transient, and duration, may be employed as a leak detector. However, leak detection may be performed by other means as well. In either case, master station 44 will show the characteristic sign of a leak on each of site stations bounding the segment on which the leak has occurred. The time synchronized display 70 will show the relative arrival time at each of the segment's site stations 12. The operator or software for each site station will be capable of determining when the first arrived "one", was received after a pressure transient (display time 76).

Referring to FIG. 1 and FIG. 3, once the arrival times are registered from each site station 12 to master station 44, master station 44 computes the location of the leak by a formula. An example of a formula which may be employed to compute the distance to a leak is shown as EQ. 1, which is based on the difference in absolute arrival times:

$$D_u = D_t(V_s^2 - V_f^2) + D_s((V_s - V_f)/2V_s)$$

where:

$D_t$=difference in absolute pressure wave site arrival times;

$D_u$=distance from upstream site station to the leak location;

$V_s$=liquid sonic propagation velocity;

$V_f$=flow velocity;

$D_s$=total pipeline segment length

It is possible to compute the leak location without knowledge of flow rate, but only at reduced accuracy. Advantageously, $V_s$ is employed in computing leak location. Those skilled in the art would understand, based on the present disclosure, how to perform an equivalent computation of leak location even when there are several batches of different liquids in the pipeline segment, each at different sonic propagation velocity.

Small leaks, resulting in smaller changes in pressure, will manifest their lower magnitude as compared to larger leaks, by the reduced amount of time that it will take for the site stations to establish a new exponential average (see, e.g., line 79 in FIG. 3). If the leak is large enough to change the sonic propagation velocity by a recognizable difference from the random "One/Zero" behavior prior to the event of the leak itself, it will be possible to identify its location accurately.

Since the sonic propagation of the liquid ranges on the order of magnitude of 1,000 meters to 1,500 meters per second, a time resolution of 1 millisecond or better in data collection permits a precision of leak location in the range of, for example, from 1 to 1.5 meters from the actual location 40 of the leak.

Master station 44 may continuously monitor pipeline 16 for leaks. This may be performed by triggering an alarm when a predetermined number of late counts are experienced. Alternately, a conventional leak detection system may be employed, which then instructs a remediation staff to determine the location of the leak. By consulting data at master station 44, particularly inspecting the data stored for the period of time at which the leak is suspected of occurring, the leak's position can be accurately determined in accordance with the present invention.

The resultant computation defines the distance, Du between either of site stations 12b or 12c to the leak location 40. Since pipelines are not always linear in their configuration, it would be advantageous to translate the distance indication into a particular longitude and latitude position.

Figure 5:
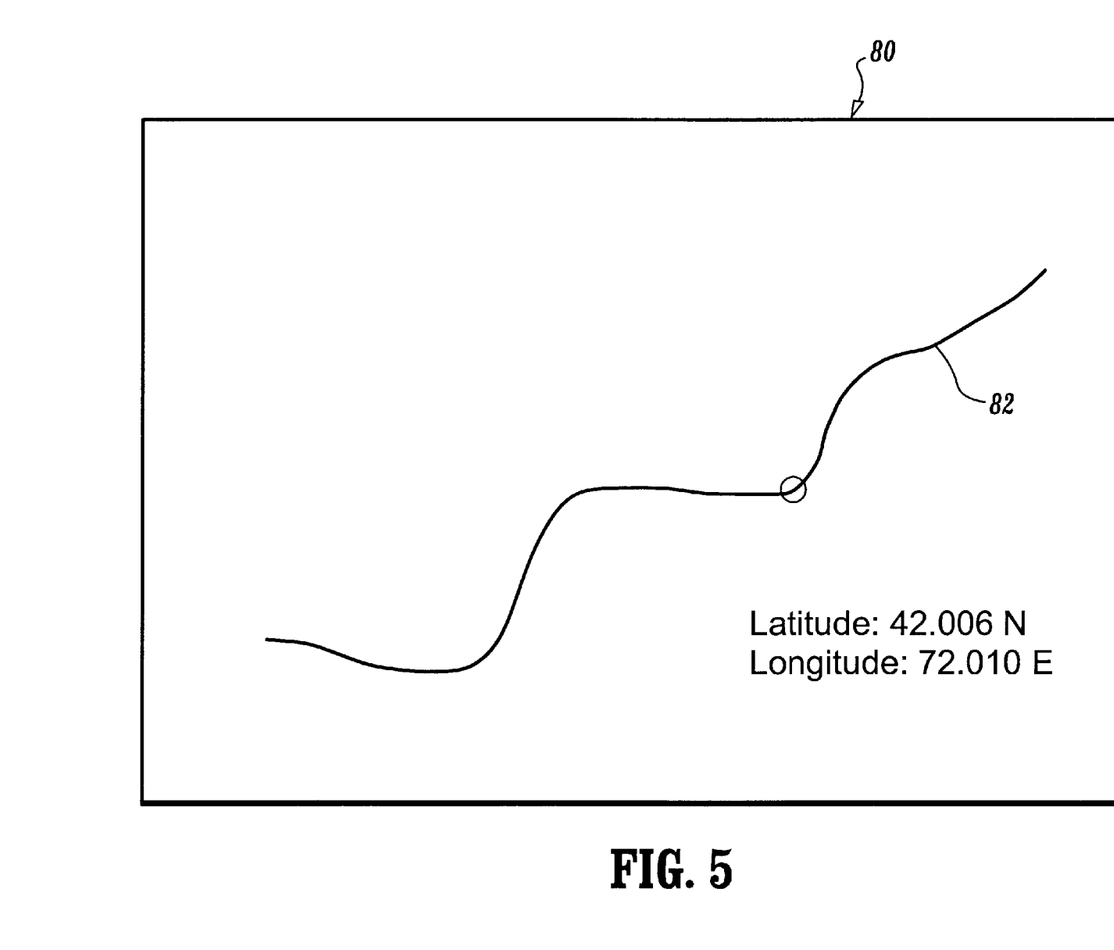
FIG. 5 shows a pipeline map which correlates distances with positions on a pipeline system in accordance with the present invention.

Referring to FIG. 5, master station 44 or other location includes a map 80 of a pipeline 82. Every point on pipeline 82 is translated into geographical coordinates, e.g., latitude and longitude. In the event of a leak, a location of the leak will be calculated and indicated on that map by a suitable marker, with the latitude and longitude displayed. Thus, an appropriate vehicle can be used to quickly transport a remediation crew to the site, by truck, helicopter, boat, etc. to remedy the leak.

By identifying the sonic propagation velocity at least at one point in time, a sequence of ones and zeros may be employed to identify the sonic propagation velocity at any time. This is useful in determining the density of the product at each site station, as would be used for interface detection or product type and quality detection.

As opposed to the behavior of liquids, gases in general do not change their sonic propagation velocity with pressure. However, a change in pressure will affect the sonic conductivity to ultrasonic pulses in gases. Since each site station can measure the amplitude of each received sonic pulse, at the same time as it measures its arrival time, the same method for leak location used for liquid flows may be employed for gas pipelines. This may be implemented by providing a one or zero output responsive to a receive signal increase or decrease in amplitude control data. This would replace the sonic propagation velocity one or zero data employed for liquids. In all other respects, the operation of the system is identical.

Figure 6:
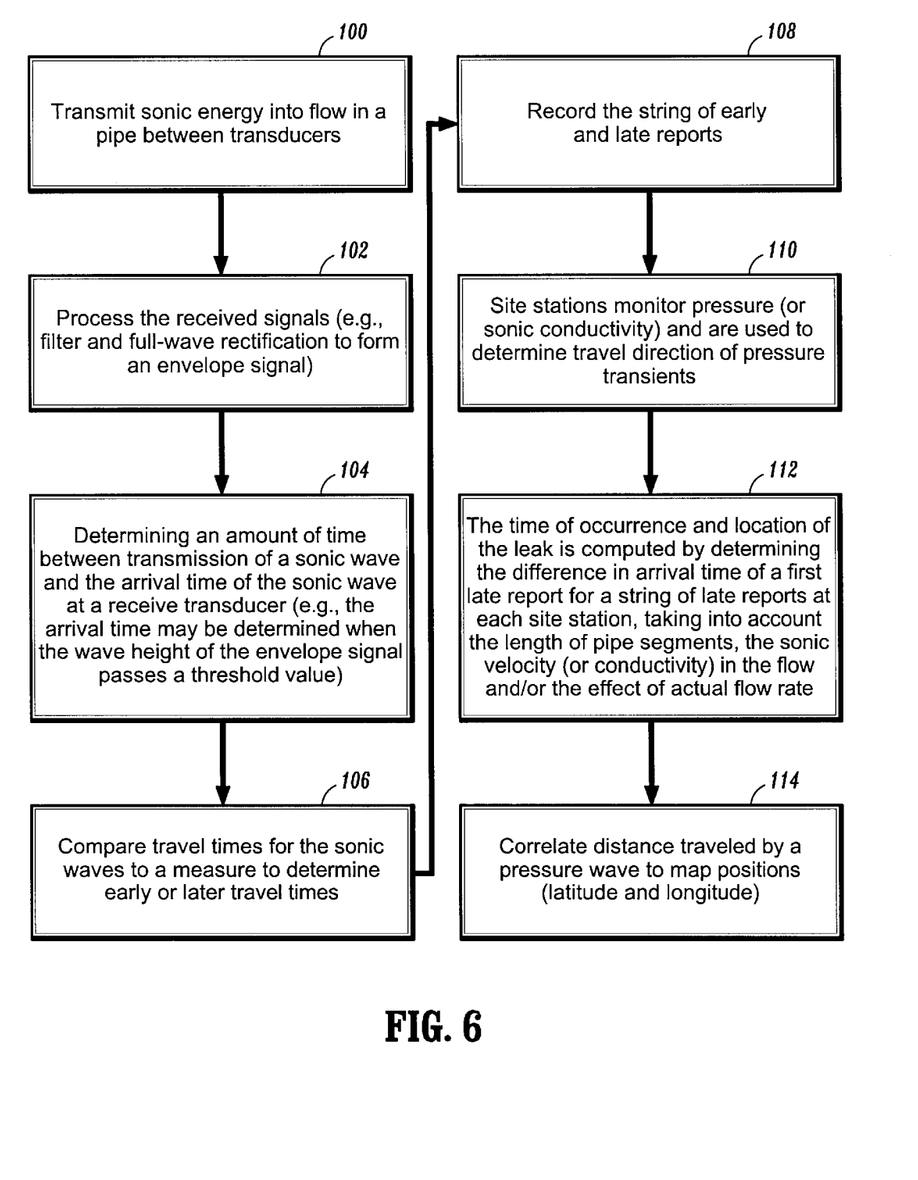
FIG. 6 is a block/flow diagram for a system/method for determining the time of occurrence of a pressure and/or detecting leaks in the pipe system in accordance with the present invention.

Referring to FIG. 6 with continued reference to FIGS. 1 and 2, a block/flow diagram for a system/method for locating a leak in a pipeline is illustratively shown. It is to be understood that the method of FIG. 6 applies equally for a gas pipeline, where sonic conductivity is employed instead of sonic velocity. In block 100, transducer 20 transmits sonic pulses 203 (FIG. 3) to transducer 22 at a predetermined rate. The transmission produces a pipe wall signal 205 (FIG. 3). In one embodiment, the predetermined rate is 1,000 times per second. Other rates may be employed and have the effect of increasing (higher rate) or decreasing (lower rate) the precision of the system on the present invention. In block 102, a reflected pipe wall signal 205 (wave 32 of FIG. 2) is received by transducer 22 which processes signal 205 to generate a receive signal 204 (FIG. 3). In one embodiment the signal 204 is full wave rectified and filtered to obtain a signal representing an envelope 202 as illustratively shown in FIG. 3.

In block 104, an amount of time between transmission of a sonic wave and the arrival time of the sonic wave at the receive transducer is determined. In one embodiment, a threshold level 206 (FIG. 3) is set which is employed to indicate when the sonic wave has arrived at transducer 22. The threshold level 206 can be set in advance based on experience, based on amplification factors of the sonic signals, based on previously received signals, or a combination of factors. When the envelope 202, marker or reference portion breaks the threshold level 206, a travel time is measured represented by T in FIG. 3. This is the travel time of the sonic waves between transducers 20 and 22.

In block 106, travel times for the sonic waves are compared to a measure to determine early or later travel times. In one embodiment, a travel time is expressed as a number of clock cycles from transmission to receipt (e.g., the envelope 202 breaking threshold line 206 in FIG. 3). Travel times can be adapted to represent sonic conductivities when gas pipelines are employed. The measure may be determined as an exponentially averaged quantity as described above. A determination is made to see if the newly arrived wave is later or early as compared to the measure.

If the sonic velocity of the liquid is stable, then it is very probable that successive late/early counts will, on average, alternate between being late and early. In other words, the counts will average out over time to have an equal number of occurrences of counts having a value less than the stored buffer value (measure) and a value more than the stored buffer value (measure). Each result is stored as a "1" (late) or a "0" (early) in, e.g., a first-in-first-out device (FIFO). A string of early and late reports is recorded and analyzed, in block 108.

If a leak has occurred, the pressure at that point usually drops, lowering the liquid density and reducing liquid sonic velocity. The low-pressure wave caused by the leak travels upstream and downstream, being read, in block 110, first by the nearest site stations 12a, and then by the further site stations 12b (FIG. 1). This permits a determination of the direction in which the pressure wave is traveling. When the wave arrives at each site station 12, the lower density and lower sonic velocity of the wave causes the receive signal to move "late." While the exponential buffer catches up to a new position or average of the receive signal (the "new" measure position), the FIFO will only receive "late" reports (e.g., a string of 1's). A string of late reports indicates the change in flow, e.g., a transient pressure wave due to a leak in pipe 16.

In block 112, the location and time of occurrence of the leak is computed by determining the difference in arrival time of a first "1" for the string of late reports (from the FIFO) at each site station, taking into account the length of each segment (e.g., distances A, B, C, etc.), the sonic velocity in the liquid and the effect of actual liquid flow rate (e.g., add the flow rate to the sonic velocity for a wave traveling with the flow, and subtracting the flow rate from the sonic velocity for a wave traveling against the flow). The digital 1's and 0's sequence or string is used to identify the occurrence. EQ. 1, set forth above, may be employed.

In one embodiment, since the sonic velocity of hydrocarbon liquids is about 1 m/s, at least a 1 meter resolution is achievable for the location of the leak. This is a significant improvement over conventional systems, which have a precision of about 150 meter to 200 meters.

While the system of the present invention will determine the linear distance from the segment's site stations where a leak has occurred, acting on this information is not simple if the pipeline is not linear. Especially on buried or underwater pipelines, locating the leak relative to its terrain markers, or its absolute location (GPS) may be needed. This is especially true if the pipeline is convoluted.

Accordingly, in block 114, distances traveled by a pressure wave along a pipeline may be correlated to map positions, e.g., latitude and longitude positions. Master station 44 (FIG. 1) may include a "Map" of the pipeline, with an algorithm that converts the distance from each surrounding Site Station to specific position, e.g., a latitude and longitude of the leak location. This may be combined with a Global Positioning System to mark the location on a GPS Map system which could guide trucks, helicopters, ships, etc. to the actual leak location.

The system and methods of the present invention may be employed to quickly identify the locations of other anomalies, which may occur in pipeline system. For example, the present invention may be employed to determine a location where a theft of product is being carried out, by, e.g., hot-tapping the pipeline. In addition, the present invention will identify the location of any pump or valve, which is being operated unsafely.

A significant advantage is provided by the use of clamp-on ultrasonic transducers, in place of using pressure sensors to determine the arrival of a low-pressure leak wave. There are many pressure transients in a pipeline, caused by pump or valve operations, and by other instruments or obstructions in the pipeline. A small diameter pressure sensor will see all of these transients, which can actually obscure the actual leak wave transient. The sonic arrival time system of the present invention integrates out all the transients that have a wavelength smaller than the liquid path length of the sonic beam injected into the pipe. Thus, the sonic system has a greater dynamic range, and is more efficient in leak detection.

Having described preferred embodiments for a novel leak locator for pipe systems (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for determining a time of occurrence of a pressure wave in a pipe, comprising the steps of:

providing a first sonic transducer and a second sonic transducer at each of a plurality of site locations along a pipe;

generating sonic waves through a pipewall at a known desired rate at each of the plurality of site locations along the pipe, the sonic waves traveling from the first sonic transducer to the second sonic transducer through a liquid flow in the pipe at each of the plurality of said site locations;

setting a measure of travel time for the sonic waves;

comparing the measure to each of the successive travel times for the sonic waves as the sonic waves arrive at the respective second transducers;

outputting a string of counts at each second transducer, each count including a first count value if a present sonic wave has a travel time that is late as compared to the measure; and determining a time of occurrence of the pressure wave based on a reference clock such that when the string of counts includes a string of first count values longer than a threshold value, the time of occurrence of a pressure transient is indicated by a first count in the string of first count values.

2. The method as recited in claim 1, wherein the first sonic transducer and the second sonic transducer are included in a clamp-on flowmeter.

3. The method as recited in claim 1, wherein the step of generating sonic waves through a pipewall at a rate includes generating sonic waves through the pipewall at a repetition rate of between about 1000 pulses per second to about 1500 pulses per second.

4. The method as recited in claim 1, further comprising the step of determining a location of a leak by computing a distance to the leak from nearby site locations based on the time occurrence, a sonic velocity of the liquid in the pipe and a measured flow rate of the liquid in the pipe.

5. The method as recited in claim 1, wherein the step of setting a measure of travel time includes setting the measure by employing the travel time of the previously received sonic wave.

6. The method as recited in claim 1, wherein the step of outputting a string of counts includes outputting a first digital value for the first count value and outputting a second digital value for travel times which are earlier than the measure.

7. The method as recited in claim 1, further comprising the steps of computing a location of the leak by:
  determining a direction of travel of the pressure wave in accordance with an arrival of the pressure wave at adjacent site locations along the pipe; and
  calculating a distance from the adjacent site locations to the leak location.

8. A method for determining a time of occurrence of a leak in a gas pipe, comprising the steps of:
  providing a first sonic transducer and a second sonic transducer at each of a plurality of site locations along a pipe;
  generating sonic waves through a pipewall at a known desired rate at each of the plurality of site locations along the gas pipe, the sonic waves traveling from the first sonic transducer to the second sonic transducer through a liquid flow in the pipe at each of the plurality of said site locations;
  setting a measure of sonic conductivity for the sonic waves;
  comparing the measure to each of the successive sonic waves for the sonic waves as the sonic waves arrive at the respective second transducers;
  outputting a string of counts at each second transducer, each count including a first count value if a present sonic conductivity is above the measure; and
  determining a time of occurrence of the pressure wave based on a reference clock such that when the string of counts includes a string of first count values longer than a threshold value, the time of occurrence of the leak is indicated by a first count in the string of first count values.

9. The method as recited in claim 8, wherein the step of determining includes the step of computing the distance to the leak from nearby site locations based on the time occurrence, a sonic velocity of the liquid in the pipe and a measured flow rate of the liquid in the pipe.

10. The method as recited in claim 8, wherein the step of setting a measure includes setting the measure by employing an average based on previously received sonic waves.

11. The method as recited in claim 8, further comprising the step of providing a synchronization device, which provides synchronization between the site locations to provide a time reference for the step of determining a time of occurrence.

12. The method as recited in claim 8, further comprising the steps of computing a location of the leak by:
  calculating a distance from adjacent site locations to the leak location.

13. The method as recited in claim 8, further comprising the step of correlating distance along the pipe to a map position.

14. A system for detecting pressure transients or sonic conductivity changes in a length of pipe, comprising:
  a plurality of site locations disposed along a pipe, each site location being disposed a predetermined distance from a corresponding pair of adjacent site stations along the pipe;
  an ultrasonic transducer system coupled to the pipe at each site location, the ultrasonic transducer system including a first sonic transducer which generates sonic waves at a known desired rate and a second sonic transducer which receives the sonic waves at each of the plurality of site locations along the pipe;
  the ultrasonic transducer system adapted to measure travel times of the sonic waves between the first and second sonic transducers and compare the travel times to a measure such that a report of each sonic wave is determined as late or early as compared to the measure; and
  a monitor which records the reports and determines if a string of late reports greater than a threshold size has occurred wherein a time of the first report of the string of late reports greater than the threshold size indicates a time of occurrence of a leak in the pipe.

15. The system as recited in claim 14, wherein the ultrasonic transducer system includes a clamp-on ultrasonic transducer system, which is detachable, coupled to a pipewall of the pipe.

16. The system as recited in claim 14, wherein the rate includes a repetition rate of between about 1000 pulses per second to about 1500 pulses per second.

17. The system as recited in claim 14, wherein a distance from the site locations to the leak location is determined based on the time occurrence and a sonic velocity of liquid in the pipe.

18. The system as recited in claim 14, wherein the measure is set by the travel time of a previously received sonic wave.

19. The system as recited in claim 14, further comprising a synchronization device, which provides synchronization between the site locations to provide a time reference for calculating a location of the leak.

20. The system as recited in claim 14, wherein a distance from the site locations to the leak location is determined based on the time occurrence and a sonic conductivity of a gas in the pipe.

* * * * *